United States Patent [19]
Slaugh et al.

[11] Patent Number: 5,936,136
[45] Date of Patent: Aug. 10, 1999

[54] PROCESS FOR SEPARATING LINEAR ALPHA OLEFINS FROM 2 BRANCHED AND/OR 3-BRANCHED ALPHA OLEFINS

[75] Inventors: Lynn Henry Slaugh, Houston; Howard Lam-Ho Fong, Sugar Land; Laurent Alain Fenouil, Houston, all of Tex.

[73] Assignee: Shell Oil Company, Houston, Tex.

[21] Appl. No.: 08/876,822

[22] Filed: Jun. 16, 1997

[51] Int. Cl.$^6$ ...................................................... C07C 7/00
[52] U.S. Cl. ............................ 585/867; 585/833; 585/809
[58] Field of Search ..................................... 585/809, 833, 585/867, 25, 26

[56] References Cited

U.S. PATENT DOCUMENTS

| | | | |
|---|---|---|---|
| 4,915,794 | 4/1990 | Slaugh et al. | 203/29 |
| 4,946,560 | 8/1990 | Slaugh et al. | 203/38 |
| 5,012,034 | 4/1991 | Weingaertner et al. | 585/806 |

OTHER PUBLICATIONS

U.S. application No. 08/987,553, Slaugh et al., filed Dec. 9, 1997.
U.S. application No. 08/987,555, Slaugh et al., filed Dec. 9, 1997.
U.S. application No. 08/987,554, Weinmann et al., filed Dec. 9, 1997.

*Primary Examiner*—Walter D. Griffin
*Attorney, Agent, or Firm*—Dennis V. Carmen

[57] ABSTRACT

Linear alpha olefins are separated from 2-branched alpha olefins and/or 3-branched alpha olefins. A feedstock of linear alpha olefins, branched alpha olefins, and internal olefins is converted to a linear alpha olefin composition having a lower concentration of branched alpha olefins than present in the feedstock by a) contacting the feedstock with anthracene under conditions effective to form a reaction mixture comprising an anthracene-linear alpha olefin adduct;

b) separating the anthracene-linear alpha olefin adduct from the reaction mixture;

c) disassociating the anthracene-linear alpha olefin adduct to form anthracene and a linear alpha olefin composition, and d) separating the anthracene formed in step c) from a linear alpha olefin composition.

20 Claims, No Drawings

PROCESS FOR SEPARATING LINEAR ALPHA OLEFINS FROM 2 BRANCHED AND/OR 3-BRANCHED ALPHA OLEFINS

FIELD OF THE INVENTION

This invention relates to a process for separating linear alpha olefins from 2-branched alpha olefins and/or 3-branched alpha olefins comprising internal olefins, linear alpha olefins, 2-branched alpha olefins, 3-branched alpha olefins, or mixtures thereof.

BACKGROUND OF THE INVENTION

Many industrial processes produce olefins that are mixtures of alpha olefins and internal olefins. Due to the similarities in properties between alpha and internal olefins of the same molecular weight or overlapping carbon numbers, it is not an easy matter to separate the two. Olefins are frequently used in the manufacture of polymers or as drilling mud additives, or as intermediates for the production of oil additives and detergents. Depending upon the particular application, it would be desirable to manufacture an alpha olefin composition having the greatest purity possible. For example, polyethylene polymers are often made by copolymerizing ethylene with small amounts of a linear alpha olefin such as 1-octene. A 1-octene olefin composition containing substantial branched species, especially on the second and/or third carbon atoms, is not suited for this purpose. The olefin needed for this purpose is one in which the branched alpha olefins are removed as much as possible. While such pure species of linear alpha olefins with a narrow carbon number range can be manufactured and provided at great cost, we have found that it would be particularly desirable to economically provide the application industry with large quantities of a purified linear alpha olefin composition made from a raw feedstock containing a mixture of at least internal olefins, linear alpha olefins, and 2-branched alpha olefins. Many feedstocks contain additional impurities such as alcohols, ketones, and 3-branched alpha olefins, from which the linear alpha olefins should be separated.

Separating and isolating linear non-branched alpha olefins from 2-branched alpha olefins and/or 3-branched alpha olefins is no easy task, especially when these species have similar or identical molecular weights or carbon numbers. Conventional distillation methods are inadequate to separate species of this type which have such closely related boiling points. The separation problem is further aggravated in that the linear non-branched alpha olefin species not only need to be separated from branched alpha olefins, but also from everything else present in the feedstock mixture, such as the internal linear or branched olefins. U.S. Pat. No. 4,946,560 described a process for the separation of internal olefins from alpha olefins by contacting a feedstock with anthracene to form an olefin adduct, separating the adduct from the feedstock, heating the adduct to produce anthracene and the olefin product enriched in alpha olefin, and separating out the anthracene from the alpha olefin. With respect to branched products, the patentee notes that the small amounts of branched products present in the feedstock will separate out in the same fashion as the internal olefins, that is, the alpha branched species will go with the alpha linear species, and be separated from the internal branched olefins which accompany the internal linear olefins, such that one obtains an alpha olefin composition and an internal olefin composition separated from each other in accordance with that invention. We have discovered, however, both the desirability to separate out linear alpha olefins from 2-branched alpha olefins and/or 3-branched alpha olefins in a raw feed stream containing these species and internal olefins, and the solution to this problem.

SUMMARY OF THE INVENTION

This invention relates to a process for separating linear alpha olefins from branched alpha olefins. In particular, there is provided a process for converting a feedstock, comprising linear alpha olefins, branched alpha olefins, and internal olefins, to a linear alpha olefin composition having a lower concentration of branched alpha olefins than present in the feedstock, comprising:

a) contacting the feedstock with anthracene under conditions effective to form a reaction mixture comprising an anthracene-linear alpha olefin adduct;

b) separating the anthracene-linear alpha olefin adduct, and optionally the unreacted anthracene as well, from the reaction mixture;

c) disassociating the anthracene-linear alpha olefin adduct to form anthracene and a linear alpha olefin composition, and d) separating the anthracene formed in step c) from a linear alpha olefin composition.

DETAILED DESCRIPTION OF THE INVENTION

A linear alpha olefin(s) means the absence of branching at both the $C_2$ and the $C_3$ positions, each relative to the alpha double bond.

A branched alpha olefin(s) means an alpha olefin having a branch at least at the $C_2$ or alternatively at the $C_3$ position, each relative to the alpha double bond. Branches at both the $C_2$ and the $C_3$ positions are within the meaning of a branched alpha olefin, as well as branches present at additional positions beyond the $C_3$ position so long as at least one branch is present at the $C_2$ and/or $C_3$ position. Alpha olefins having branches at only the $C_3$ position, or only at the $C_2$ position, are also within the meaning of a branched alpha olefin.

A branched olefin is an alpha olefin or an internal olefin having a branch at least at the $C_2$ and/or the $C_3$ position.

The feedstock olefins preferably used in the process of the invention comprise internal olefins, branched alpha olefins, and linear alpha olefins. By internal olefins is meant linear and/or branched internal olefins. The feedstock is generally produced by commercial processes such as the oligomerization of ethylene, followed by isomerization and disproportionation. Alternatively, the feedstock may be produced by the Fisher-Tropsch process, which contains a substantial number of branched species.

The amount of branched alpha olefins, internal olefins both linear and branched, and linear alpha olefins, present in the feedstock is not particularly limited. In fact, the feedstock may contain as little as 1 wt. % of internal olefins. However, the process of the invention is particularly suited to produce on an industrial scale linear alpha olefin compositions needed in those applications which are sensitive to the presence of branched alpha olefins in an amount beyond about 3 wt. %. Accordingly, in a preferred embodiment of the invention, the feedstock to be treated according to the process of the invention contains at least 2 wt. % of branched alpha olefins, especially those which contain 3 wt. % or more of branched alpha olefins. However, the process of the invention will also advantageously separate the branched internal olefins along with the branched alpha olefins and linear internal olefins from the linear alpha olefins. For many applications, the presence of branching at the $C_2$ or $C_3$ position, whether on an internal or on an alpha olefin, is undesirable. Therefore, to ensure the highest product quality, in a highly preferred embodiment of the invention, the separation operation should be carried out on feedstocks which contain a total of 3 wt. % or more of branched olefins, whether the olefin is internal or alpha, or the branching is on $C_2$ or the $C_3$ position, based on the weight of the feedstock. The invention, however, is not limited to carrying out the separation/purification steps on feedstocks containing more that 3 wt. % of branched olefins. Feedstocks containing as little as 1 wt. % of branched olefins or 1 wt. % of branched alpha olefins can also be successfully treated to further reduce the branched alpha olefin content where needed for some applications (and even if not particularly needed for an application). The need for treating feedstock streams already so low in branched olefins is not as pressing, however, since a fair portion of applications desiring pure alpha olefin compositions can tolerate these low levels of branched olefins.

Generally, the feedstock will not contain more than 85 wt % of branched alpha olefins, based on the weight of the feedstock, although the particular amount will often vary with the method of manufacturing the feedstock, such as by oligomerizing ethylene or by the Fisher-Tropsch process. Typically, the amount of branched alpha olefins present in the feedstock will not exceed 50 wt. %, based on the feedstock weight. More common amounts of branched alpha olefin in feedstocks ranges from 5 wt. % to 40 wt. %.

The amount of branched internal olefins in the feedstock is not limited. The feedstock may contain from 0 wt. % to 30 wt. % of branched internal olefins, while amounts ranging from 1 wt. % to 15 wt. % are common.

The amount of linear internal olefins is not limited, and can range from 0.0 wt. % to 80 wt. %, with amounts ranging from 1 wt. % to 20 wt. % being common.

The amount of linear alpha olefins in the feedstock can widely vary, and may range from 5 wt. % to 97 wt. %. While the feedstock may contain less than 5 wt. % of linear alpha olefins, isolating less than 5 wt. % of linear alpha olefins obtained in the separation process may not be justified. The feedstock should preferably contain at least 10 wt. %, more preferably at least 15 wt. %, most preferably at least 20 wt. % of the linear alpha olefin. In those cases where a feedstock is produced by a Fisher-Tropsch process, the feedstock will generally contain less than 50 wt. % of linear alpha olefins.

Other ingredients which may be present in the feedstock include aromatic compounds, paraffins, and oxygenated compounds. These other ingredients may be present in the feedstock in amounts ranging from 0 wt. % to 50 wt. %.

Typically the feed olefins will have a carbon number ranging from about 4 to about 22, more preferably from about 6 to about 18. The physical properties demanded by the end use of the olefins in part determines the suitable carbon numbers to be isolated. Olefins with carbon numbers greater than 22 and lower than 6 can be utilized in the instant process, but from a commercially practical point of view, feedstocks with carbon numbers ranging from about 6 to about 18 will be most frequently used. For example, linear alpha olefins having carbon numbers of 4–8 are commonly used as comonomers in the manufacture of polyethylenes, linear alpha olefins having a carbon number ranging from 8–12 are commonly used to make polyalphaolefins, and alpha olefins having carbon numbers in the range of 12–18 are used as intermediates in the manufacture of detergents.

Anthracene is utilized in the instant process to form the adduct with the alpha olefins in the feedstock. While not being bound to a theory, it is believed that the anthracene preferentially forms an adduct with the linear alpha olefins and to a lesser extent, if at all, with the 2-branched alpha olefins. The preferential adduction of anthracene toward the linear alpha olefin over the branched alpha olefins or internal olefins may be due to the steric hindrance and/or electronic effects of the latter olefins in a Diels-Alder reaction.

As used herein, "anthracene" refers to a linear polycyclic three aromatic ring molecule having 14 ring carbon atoms, as well as a linear polycyclic three aromatic ring molecule with 14 aromatic ring carbon atoms which is substituted and possesses similar adducting properties as the unsubstituted molecule, and mixtures thereof. "Anthracene" also refers to mixtures of compounds containing as one of their ingredients anthracene, including but not limited to coal tars, anthracene oil, and any crude mixtures containing cuts separated from naphthalene. "Anthracene" further refers to an anthracene molecule having one or more of the 14 aromatic ring carbon atoms replaced with a suitable polyvalent heteroatom, resulting in a three aromatic ring molecule with less than 14 aromatic ring carbons. Suitable examples of substituents on substituted anthracenes include, but are not limited to, lower alkyl, e.g., methyl, ethyl, butyl; halo, e.g., chloro, bromo, fluoro; nitro; sulfato; sulfonyloxy; carboxyl; carbo-lower-alkoxy, e.g., carbomethoxy, carbethoxy; amino; mono- and di-lower-alkylamino, e.g., methylamino, dimethylamino, methylethylamino; amido; hydroxy; cyano; lower-alkoxy, e.g., methoxy, ethoxy; loweralkyanoyloxy, e.g., acteoxy; monocyclic aryls, e.g., phenyl, xylyl, toluyl, benzyl, etc. The particular substituent size, their number, and their location, should be selected to that they are relatively inert under the reaction conditions and relatively small to avoid sterically hindering the formation of the Diels-Alder adduct. Suitable substituted anthracenes can be determined by routine experimentation. 9,10-dimethylanthracene, 9,10-dichloroanthracene, 9-methylanthracene, and unsubstituted anthracene have been found to work quite well. Other suitable substituted anthracenes include 9-acetylanthracene, 9-(methylaminomethyl)anthracene, 2-choloranthacene, acridine, 2ethyl-9,10-dimethoxyanthracene, phenazine, anthrarobin, and 9-anthryl trifluormethyl ketone. A class of heteroatom containing anthracene molecules is acridine and phenazine.

Anthracene also includes anthracene molecules linked together by a bridging group, such as a hydrocarbon chain, an ether linkage, or a ketone group containing chain.

The process of the instant invention is basically a three step process wherein (a) anthracene is reacted with an olefin composition to form an adduct, (b) the adduct is separated from the reaction mixture, and (c) the adduct is dissociated to release the olefin and regenerate the anthracene. The Diels-Alder adduct forming reaction is carried out in a conventional fashion and reaction zone. An example of a suitable reaction zone is a continuously stirred tank reactor wherein olefin and anthracene are added continuously to a stirred tank, and the reaction mixture is continuous withdrawn from the stirred tank. Alternatively, the reaction may be carried out in a batch reactor, wherein the olefin and the anthracene are charged to an autoclave which is then heated to a reaction temperature sufficient to complete the reaction. The reaction is typically carried out over a range of temperatures from about 150° to about 290° C., preferably from about 200° to about 280° C., and most preferably from about 240° to about 265° C. Pressures are not critical and typically run from about atmospheric to about 100 atmospheres. The reaction can be carried out in the gas phase under vacuum or liquid phase or mixed gas-liquid phase, depending on the volatility of the feed olefins, but generally in the liquid phase.

Stoichiometric proportions or an excess of either olefin or anthracene can be used in forming the adducts, but a molar excess of olefin is preferred. The molar ratio of olefin to anthracene is preferably from greater than 1:1 up to 10:1, more preferably from 1.5:1 to 7:1.

An inert solvent can be utilized to dissolve the feed olefins or the anthracene or both in the reactor. Preferred solvents are the hydrocarbon solvents which are liquid at reaction temperatures and in which the olefins, anthracene and olefin-anthracene adducts are soluble. Illustrative examples of useful solvents include the alkanes such as pentane, isopentane, hexane, heptane, octane, nonane, and the like; cycloalkanes such as cyclopentane, cyclohexane, and the like; and aromatics such as benzene, toluene, ethylbenzene, diethylbenzene, and the like. The amount of solvent to be employed can vary over a wide range without a deleterious effect on the reaction.

In one embodiment of the invention, however, the feedstock and anthracene anthracene-linear alpha olefin adduct formation is carried out in the absence of a solvent. We have found that the absence of a solvent does not substantially affect the amount of anthracene regenerated under equivalent reaction conditions, and that the concentration of linear alpha olefins generated is substantially the same. Thus, in a preferred embodiment, the process of the invention is conducted in the absence of a solvent.

After the anthracene-olefin adduct has been formed, it is separated from the reaction mixture. The olefin-anthracene adduct is separated from the reaction mixture by conventional means. Due to the large molecular weight and structural difference between the anthracene-linear alpha olefin adduct and the remainder of the reaction mixture, conventional separation techniques are quite suitable for removing the unreacted olefins from the anthracene-linear alpha olefin adduct. For example, the unreacted olefins may be removed at the overhead or in fractions by vacuum or flash distillation of the reaction mixture to leave the anthracene-linear alpha olefin adduct and unreacted anthracene as a liquid bottoms. The other unreacted components of the reaction mixture, such as the unreacted olefins, including branched and linear internal olefins, 2-branched alpha olefins and/or 3-branched alpha olefins, as well as paraffins, aromatics, alcohols, ketones, acids, and other impurities may be distilled off. Alternatively, the anthracene-linear alpha olefin adduct is separated by cooling the adduct crystallizes out, followed by filtration or centrifugation to remove the unreacted olefin. In most cases the unreacted anthracene will separate out with the anthracene-linear alpha olefin adduct. The remainder of the reaction mixture can be used in other processes or applications since is will have an enriched internal olefin content over that of the feedstock.

The next step of the instant process is to dissociate the anthracene-linear alpha olefin adduct. The dissociation process can be accomplished by heating or pyrolyzing the recovered anthracene-linear alpha olefin adduct at a temperature of from about 250° to about 400° C., preferably from about 300° to about 350° C. This pyrolysis frees the linear alpha olefins from the anthracene. The anthracene is then separated from the resulting mixture by any conventional means, which may occur simultaneously with the pyrolysis operation, such as by vacuum or flash distilling off the linear alpha olefins along with any impurities at the pyrolysis temperatures, and removing the anthracene as a bottoms from the breaking zone. Other separation techniques include filtration and centrifugation. The anthracene may be recycled back to the adduct reaction zone. The separated linear alpha olefin composition is enriched in linear alpha olefin content over that of the feedstock, and the concentration of the branched alpha olefins in the linear alpha olefin composition is reduced over that of the feedstock.

While most of the branched alpha olefins will have been separated from the linear alpha olefins, a small amount of branched alpha olefins, along with other impurities may be present in the final linear alpha olefin composition. For many applications, the amount of branched alpha olefins in the linear alpha olefin composition after one pass through the process of the invention is sufficiently small that only one pass through the process is necessary. If desired, however, the linear alpha olefin composition may be subjected to multiple passes through additional reaction zone and breaking zone reactors fed by the linear alpha olefin composition produced from the prior pass, to further reduce the branched alpha olefin content and further enhance the linear alpha olefin content. In a preferred embodiment, the process of the invention is repeated more than once, more preferably 2–4 times.

The amount of branched alpha olefins in the linear alpha olefin composition is less than 3 wt. % after subjecting the feedstock to the process of the invention. Preferably, the amount of branched alpha olefins, especially the amount of 2-branched alpha olefin, in the linear alpha olefin composition is 2.5 wt. % or less, more preferably 2.0 wt. % or less, most preferably 1.5 wt. % or less. With multiple passes, the content of the branched alpha olefins, and especially the amount of 2-branched alpha olefins, can be reduced in the linear alpha olefin composition to 1.0 wt. % or less, more preferably 0.7 wt. % or less, most preferably 0.5 wt. % or less.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention.

The present invention will now be illustrated by means of the following illustrative embodiments and examples which are provided for illustration and are not to be construed as limiting the invention.

EXAMPLE 1

To illustrate the concept of the invention, an eight carbon olefin composition was used as the feedstock. The amounts and types of feedstock and unsubstituted anthracene charged to a 100 ml. Parr autoclave are set forth in Table 1 below. Anthracene was charged to the autoclave, purged three times with nitrogen, and sealed. The autoclave was placed in a dry box and a nitrogen purged feedstock was added to the autoclave along with 20 ml. of dry, nitrogen-purged toluene, except where otherwise noted in Table 1. The autoclave was sealed, removed from the dry box, placed in a heating mantle and heated to the desired temperature for the indicated time. The autoclave contents were stirred during heating. The autoclave was then cooled to 20° C. The unreacted, excess olefin feedstock was removed by distillation from the product mixture. The remaining unconverted anthracene and the anthracene-linear alpha olefin adduct mixture was then heated to 300-350° C. for about 0.5 hours, during which time the anthracene-linear alpha olefin adduct disassociated to recyclable anthracene and the alpha olefin product enriched in 1-octene content.

This linear alpha olefin composition was analyzed by gas chromatography. The results are shown in Table 1. The concentration of the species within the feedstock and within the resulting linear alpha olefin composition are measured by mole percent.

Additional experiments were carried out to vary the molar ratio of anthracene to feedstock, vary the time of reaction, vary the temperature, conduct the reaction in the absence of solvent, and use multiple passes using the same prior process and procedure.

shows that a one hour residence time is adequate to reduce the amount of 2-branched alpha olefins to an acceptable level.

Runs 12–15 demonstrate that a wide molar ratio range of anthracene to olefin feedstock may be used. Example 16 utilized as a feedstock the olefin products from previous examples, labeled as the Recycle Feedstock C. The amount of desired linear alpha olefin content can be further enhanced by recycling the initial product through anthracene-linear alpha olefin adduct formation and anthracene-linear alpha olefin adduct decomposition as outlined above. Very pure non-branched linear alpha olefins can be obtained by multiple passes through the process.

EXAMPLE 2

In this example, the linear alpha olefin, 1-octene, is enriched from a low concentration of linear alpha olefin to

TABLE 1

| Run Number | Anthracene moles | Olefin Feedstock moles | Temp ° C. | Time Hrs | Anthracene Conversion % | 2-Methyl-1-heptene mole % | 1-Octene mole % | Trans-4-octene mole % | Trans-2-octene mole % | Olefin Recovery % | Comment |
|---|---|---|---|---|---|---|---|---|---|---|---|
| Feedstock Composition A | | | | | | 8.0 | 72.0 | 9.6 | 10.4 | BY GC ANALYSIS | |
| 1 | .054 | .212 | 230 | 22 | 100 | 2.0 | 87.1 | 3.6 | 7.3 | N/A | — |
| 2 | .054 | .212 | 225 | 7.5 | 63.1 | 1.8 | 92.9 | 1.8 | 3.5 | 90 | — |
| 3 | .054 | .212 | 235 | 7.5 | 81.8 | 1.4 | 93.2 | 1.8 | 3.6 | 96 | — |
| 4 | .054 | .212 | 245 | 7.5 | 86 | 1.0 | 93.3 | 1.8 | 3.9 | 93 | — |
| 5 | .054 | .212 | 255 | 7.5 | 84.3 | 0.8 | 93.3 | 1.8 | 4.1 | 94 | — |
| 6 | .054 | .212 | 255 | 5.0 | 80 | 0.9 | 93.4 | 1.8 | 3.9 | 96 | — |
| 7 | .054 | .212 | 255 | 3.0 | 76 | 1.2 | 93.2 | 1.8 | 3.8 | 95 | — |
| 8 | .054 | .212 | 255 | 1.0 | 57 | 1.9 | 91.2 | 2.4 | 4.5 | 98 | — |
| Feedstock Composition B | | | | | | 7.8 | 72.1 | 9.6 | 10.5 | BY GC ANALYSIS | |
| 9 | .108 | .212 | 255 | 3 | 68 | 1.5 | 92.1 | 2.1 | 4.3 | 92 | — |
| 10 | .108 | .212 | 255 | 5 | 75 | 1.2 | 92.0 | 2.2 | 4.6 | 93 | — |
| 11 | .108 | .212 | 255 | 1 | 45 | 1.7 | 92.5 | 1.9 | 3.9 | 93 | — |
| 12 | .108 | .212 | 255 | 1 | 58.5 | 1.9 | 91.8 | 2.1 | 4.2 | 93 | No Solvent |
| 13 | .108 | .212 | 265 | 1 | 67 | 1.6 | 92 | 2.1 | 4.3 | 94 | No Solvent |
| 14 | .150 | .212 | 255 | 1 | 53.6 | 1.9 | 91.7 | 2.1 | 4.3 | 95 | No Solvent |
| 15 | .150 | .150 | 255 | 1 | 48 | 2.1 | 90.9 | 2.4 | 4.6 | 96 | No Solvent |
| RECYCLE FEEDSTOCK COMPOSITION C | | | | | | 1.6 | 92.2 | 2.0 | 4.2 | BY GC ANALYSIS | |
| 16 | .108 | .212 | 255 | 1 | 64 | 0.3 | 97.8 | 0.4 | 1.5 | | No Solvent |

The results tabulated in Table 1 indicate that the process of the invention successfully separated out the 2-branched alpha olefins from the linear alpha olefins. As be seen from the results, the mole percent of the 2-methyl-1-heptene branched alpha olefins was substantially reduced from the amount contained in the feedstocks, and the mole percent of the desired linear alpha olefin 1-octene was substantially raised over that of the feedstock.

Comparison of runs 2–5 also indicates that by increasing the reaction temperature or increasing the residence time also increased the conversion of the anthracene without significantly affecting the selectivity of the reaction. Run 8 a very high concentration of linear alpha olefin by repeating the process of the invention in multiple passes using as a new feedstock the product of the previously treated olefin. The same procedure as in example 1 was followed, with the following particulars: the concentration of anthracene employed was 0.108 mmoles, the amount of olefin at each new pass was 0.212 mmoles, the reaction temperature throughout was 255° C., the reaction time of adduct formation was 1.0 hours, no solvent was used, and each new pass employed the feedstock product of the immediately prior pass. By staging the process in this manner, the 2-methyl-1-heptene was reduced from 26.8% to near 0%, and the desired linear olefin 1-octene was enriched from 19.2% to 98.4%.

TABLE 2

| | ANTHRACENE CONVERSION % | 2-METHYL-1-HEPTENE MOLE % | 1-OCTENE MOLE % | TRANS-4-OCTENE MOLE % | TRANS-2-OCTENE MOLE % |
|---|---|---|---|---|---|
| BEGINNING OLEFIN FEEDSTOCK COMPOSITION | — | 26.8 | 19.2 | 26.7 | 27.3 |
| FIRST STAGE OLEFIN PRODUCT COMPOSITION | 38 | 12.7 | 51.0 | 12.6 | 23.7 |
| SECOND STAGE OLEFIN PRODUCT | 52.5 | 3.8 | 81 | 3.4 | 11.8 |

TABLE 2-continued

|  | ANTHRACENE CONVERSION % | 2-METHYL-1-HEPTENE MOLE % | 1-OCTENE MOLE % | TRANS-4-OCTENE MOLE % | TRANS-2-OCTENE MOLE % |
|---|---|---|---|---|---|
| COMPOSITION THIRD STAGE OLEFIN PRODUCT COMPOSITION | 66.5 | 0.8 | 94.1 | 0.7 | 4.4 |
| FOURTH STAGE OLEFIN PRODUCT COMPOSITION | 69 | — | 98.4 | — | 1.6 |

EXAMPLE 3

The examples in Table 3 show that olefin feedstocks containing linear alpha olefins and alpha olefins having a methyl branch at either the 2-position (run 17) or the 3-position (run 18) are enriched in the linear alpha olefin content by the procedure of the invention. The same procedure as in example 1 was followed, with the following particulars: the reaction time for anthracene-linear alpha olefin adduct formation was 1 hour and the reaction temperature was 255° C.

TABLE 3

| Run Number | Anthracene moles | Olefins feedstock moles | Anthracene conversion % | 1-Hexene mole % | 2-Methyl-1-pentene mole % | 3-Methyl-1-pentene mole % | Olefin recovery % |
|---|---|---|---|---|---|---|---|
| Feedstock Composition For Run 17 |  |  |  | 89.9 | 10.1 | — | — |
| 17 | 0.108 | 0.212 | 57.2 | 99.9 | 0.1 | — | 90 |
| Feedstock Composition For Run 18 |  |  |  | 89.7 | — | 10.3 | — |
| 18 | 0.108 | 0.212 | 54 | 97.3 | — | 2.7 | 91 |

EXAMPLE 4

The runs in Table 4 show that substituted anthracenes function like unsubstituted anthracene for the recovery of alpha olefins from feeds containing branched alpha olefins. The same procedure as in example 1 was followed, with the reaction conditions specified in the Table 4.

TABLE 4

| Run Number | Substituted Anthracene moles | Olefin Feedstock moles | Temp ° C. | Time Hours | Substituted Anthracene Conversion % | 2-Methyl-1-heptene mole % | 1-Octene mole % | Trans-4-octene | Trans-2-octene | Olefin Recovery | Comment |
|---|---|---|---|---|---|---|---|---|---|---|---|
|  | Feedstock Composition |  |  |  |  | 7.8 | 72.1 | 9.6 | 10.5 | — | — |
| 19 | 9-Methyl-Anthracene 0.054 | 0.108 | 255 | 1 | 60 | 1.2 | 93.9 | 1.2 | 3.7 | 95 | Toluene Solvent 10 ml |
| 20 | 9,10-Dichloro-Anthracene 0.054 | 0.108 | 255 | 1 | 86 | 1.6 | 89.5 | 1.7 | 6.6 | 94 | Toluene Solvent 10 ml |

EXAMPLE 5

As illustrated by the data of Table 5, a mixture of alpha olefins having several different carbon numbers can be used as feedstocks. The experimental conditions are the same as in Example 1. 0.213 moles of the mixed olefin feedstock were used per 0.108 moles of anthracene. Reaction time and temperature of adduct formation was 1.0 hours at 255° C., respectively. The single pass procedure converted the olefin feedstock comprised of 11% 2-methyl-1-olefins and 89% 1-olefins to a product containing only 3% or the undesired 2-methyl-1-olefins and 97% of the desired linear 1-olefins.

TABLE 5

| Olefin Mixture Composition | Alpha Olefin Feedstock, mole % | Olefin Product, mole % |
|---|---|---|
| 2-methyl-1-pentene | 2.1 | 0 |
| 1-hexene | 22.3 | 25.8 |
| 2-methyl-1-heptene | 3.6 | 1.0 |

TABLE 5-continued

| Olefin Mixture Composition | Alpha Olefin Feedstock, mole % | Olefin Product, mole % |
|---|---|---|
| 1-octene | 29.2 | 30.6 |
| 2-methyl-1-undecene | 5.3 | 2.0 |
| 1-dodecene | 37.5 | 40.6 |

TABLE 5-continued

| Olefin Mixture Composition | Alpha Olefin Feedstock, mole % | Olefin Product, mole % |
|---|---|---|
| TOTAL 2-METHYL-1-OLEFINS | 11 | 3.0 |
| TOTAL 1-OLEFINS | 89 | 97.0 |

What we claim is:

1. A process for converting a feedstock comprising linear alpha olefins, branched alpha olefins, and internal olefins, to a linear alpha olefin composition having a lower concentration of branched alpha olefins than present in the feedstock, comprising:
   a) contacting the feedstock with anthracene under conditions effective to form a reaction mixture comprising an anthracene-linear alpha olefin adduct;
   b) separating the anthracene-linear alpha olefin adduct from the reaction mixture;
   c) disassociating the anthracene-linear alpha olefin adduct to form anthracene and a linear alpha olefin composition, and
   d) separating the anthracene formed in step c) from a linear alpha olefin composition.

2. The process of claim 1, wherein the feedstock is contacted with anthracene at a temperature ranging from 150° to about 290° C.

3. The process of claim 2, wherein the feedstock is contacted with anthracene at a temperature ranging from about 220° to about 265° C.

4. The process of claim 1, wherein the molar ratio of olefins in the feedstock to anthracene ranges from greater than 1:1 to 7:1.

5. The process of claim 1, wherein the anthracene-linear alpha olefin adduct is disassociated by heating the anthracene-linear alpha olefin adduct to a temperature ranging from about 250° C. to 400° C.

6. The process of claim 5, wherein the anthracene-linear alpha olefin adduct is heated to a temperature ranging from about 300° C. to 350° C.

7. The process of claim 1, wherein the separations are carried out by vacuum or flash distillation.

8. The process of claim 1, wherein the feedstock comprises 1 wt. % or more of branched alpha olefins.

9. The process of claim 1, wherein the feedstock is contacted with the anthracene in the absence of a solvent.

10. The process of claim 1, wherein steps a)–d) are repeated more than once.

11. The process of claim 1, wherein the amount of branched alpha olefins in the linear alpha olefin composition after one pass is less than 3 wt. %.

12. The process of claim 11, wherein the amount of branched alpha olefins in the linear alpha olefin composition after one pass is 2.0 wt. % or less.

13. The process of claim 12, wherein the amount of branched alpha olefins in the linear alpha olefin composition after one pass is 1.5 wt. % or less.

14. The process of claim 1, wherein the steps a)–d) are repeated more than once, and the content of the branched alpha olefins in the alpha olefin composition after the final pass is 1.0 wt. % or less.

15. The process of claim 14, wherein the final content of branched alpha olefins in the alpha olefin composition after the final pass is 0.7 wt. % or less.

16. The process of claim 1, wherein the feedstock comprises 5 wt. % to 97 wt. % of linear alpha olefins.

17. The process of claim 16, wherein the feedstock comprises 20 wt. % to 97 wt. % of linear alpha olefins.

18. The process of claim 1, wherein the average carbon number of the feedstock olefins ranges from 4 to 18.

19. The process of claim 1, wherein the average carbon number of the feedstock olefins ranges from 6 to 18.

20. The process of claim 1, wherein the amount of branched alpha olefin in the feedstock is at least 3 wt. %.

* * * * *